US008563555B2

(12) United States Patent
Wieser et al.

(10) Patent No.: US 8,563,555 B2
(45) Date of Patent: Oct. 22, 2013

(54) PHARMACEUTICAL COMPOSITIONS CONTAINING A CRYSTALLINE FORM OF POSACONAZOLE

(75) Inventors: Josef Wieser, Kundl (AT); Arthur Pichler, Kundl (AT); Andreas Hotter, Kundl (AT); Ulrich Griesser, Innsbruck (AT); Christoph Langes, Innsbruck (AT); Christian Laschober, Kundl (AT)

(73) Assignee: Sandoz AG, Basel (CH)

( * ) Notice: Subject to any disclaimer, the term of this patent is extended or adjusted under 35 U.S.C. 154(b) by 143 days.

(21) Appl. No.: 12/993,297

(22) PCT Filed: May 28, 2009

(86) PCT No.: PCT/EP2009/056574
§ 371 (c)(1),
(2), (4) Date: Nov. 18, 2010

(87) PCT Pub. No.: WO2009/147075
PCT Pub. Date: Dec. 10, 2009

(65) Prior Publication Data
US 2011/0105525 A1 May 5, 2011

Related U.S. Application Data

(60) Provisional application No. 61/130,720, filed on Jun. 2, 2008.

(30) Foreign Application Priority Data

Jun. 2, 2008 (EP) ..................................... 08157435

(51) Int. Cl.
*A61K 31/497* (2006.01)
*A61K 31/41* (2006.01)
*A61K 31/335* (2006.01)
*A01N 43/64* (2006.01)
*A01N 43/02* (2006.01)

(52) U.S. Cl.
USPC .......................... 514/252.1; 514/383; 514/449

(58) Field of Classification Search
USPC ............... 514/525.01, 254.06, 383, 384, 449, 514/252.1
See application file for complete search history.

(56) References Cited

U.S. PATENT DOCUMENTS

| 4,533,254 | A | 8/1985 | Cook |
| 4,957,730 | A | 9/1990 | Bohn |
| 5,625,064 | A | 4/1997 | Andrews |
| 5,834,472 | A | 11/1998 | Sangekar |
| 5,972,381 | A | 10/1999 | Sangekar |
| 6,713,481 | B1 | 3/2004 | Andrews |
| 6,958,337 | B2 | 10/2005 | Andrews |

FOREIGN PATENT DOCUMENTS

| EP | 1021439 B1 | 4/1999 |
| EP | 2130540 A1 | 12/2009 |
| EP | 2141159 A1 | 1/2010 |
| WO | 95/17407 A1 | 6/1995 |
| WO | 96/38443 A1 | 12/1996 |
| WO | 99/18097 A | 4/1999 |
| WO | 02/80678 A1 | 10/2002 |
| WO | 2005117831 A1 | 12/2005 |
| WO | 2006130177 A | 12/2006 |
| WO | 2007143390 A | 12/2007 |
| WO | 2011003992 A1 | 1/2011 |

OTHER PUBLICATIONS

International Preliminary Report on Patentability and Written Opinion of Searching Authority dated Jun. 12, 2010.
Saksena, Novel Analogs of Sch 51048; Synthesis and Preliminary Structure Activity Relationships, Abstracts of the 35th Interscience Conference on Antimicrobial Agents and Chemotherapy, Sep. 1995, San Francisco, CA.
International Search Report (for co-pending WO 2010/000668 mailed Sep. 1, 2009).
Caira M R, "Crystalline Polymorphism of Organic Compounds", Topics in Current Chemistry, Springer, Berlin, DE, vol. 198, Jan. 1, 1998, p. 163-208.
Hanawalt, Industrial and Engineering Chemistry, Vpl. 10, No. 9, pp. 457-512 (Sep. 15, 1938).
Chinese Office Action issued in counterpart application, Dec. 2011.
International Search Report (mailed Dec. 2, 2009) and Written Opinion of International Searching Authority (mailed Dec. 2, 2009).
W. Nernst, Z. Phys. Chem. 47 (1904), pp. 52-55.
Remington's Pharmaceutical Sciences, 15th Ed., Mack Publishing Co., New Jersey (1991).
Saksena A. K. et al., "Stereoselective Grignard additions to N-formyl hydrazone: a concise synthesis of Noxafil<R> side chain and a synthesis of Noxafil <R>", Tetrahedron Letters, Elsevier, Amsterdam, vol. 45, No. 44, Oct. 25, 2004, p. 8249-8251, figure 4.
Bennett et al., "Hydroxylated analogues of the orally active broad spectrum antifungal, Sch 51048 (1), and the discovery of posaconazole" Bioorganic & Medicinal Chemistry Letters, Pergamon, Elsevier Science, GB, vol. 16, No. 1, Jan. 1, 2006, p. 186-190.
Zhou, Weicheng et al., "Progress in syntheses of azole antifungal agents" Zhongguo Yiyao Gongye Zazhi, 37(2), p. 125-133 Coden: Zygzea; ISSN: 1001:8255, 2006.
Saksena, A.K. et al., "Advances in the chemistry of novel broad-spectrum orally active azole antifungals: recent studies leading to the discovery of SCH 56592" Special Publication—Royal of Society of Chemistry, 198 (Anti-Infectives), p. 180-199, 1997.
US-Pharmacopeia (USP), 2009, method 429.
European Pharmacopeia (EP), 2008, method 2.9.31.
Medema J, Campagne A.: A Simple Method to Determine Cumulative Surface-Area Distributions of Porous Solids; Journal of Catalysis, vol. 8, Issue 2, pp. 120, 1967.
US-Pharmacopeia (USP), 2009, method 711.
Product Information for Noxafil (Posaconazole), (2006).
Noxafil FDA Approval History, Jul. 13, 2004.
Translation of Chinese Office Action issued in counterpart application No. 200980119683.X, Sep. 6, 2012.

*Primary Examiner* — Yong Chong
(74) *Attorney, Agent, or Firm* — Jeffrey S. Melcher; Manelli Selter PLLC (57) ABSTRACT

The present invention relates to a pharmaceutical composition comprising crystalline form Y of posaconazole. The pharmaceutical composition can be used to treat or prevent fungal infections.

9 Claims, 4 Drawing Sheets

PHARMACEUTICAL COMPOSITIONS CONTAINING A CRYSTALLINE FORM OF POSACONAZOLE

CROSS-REFERENCE TO RELATED APPLICATIONS

This application is a national stage entry under 35 U.S.C. 371 of International Application No. PCT/EP2009/056574, filed 28 May 2009, designating the United States. This application claims foreign priority under 35 U.S.C. 119 and 365 to European Patent Application No. 08157435.2, filed 2 Jun. 2008. This application claims domestic priority under 35 U.S.C. 120 and 365 to U.S. Provisional Application No. 61/130,720, filed 2 Jun. 2008. The complete contents of these applications are incorporated herein by reference.

FIELD OF THE INVENTION

The present invention relates to pharmaceutical compositions comprising crystalline form Y of posaconazole as an active pharmaceutical ingredient. The pharmaceutical composition can be used to treat or prevent fungal infections.

BACKGROUND OF THE INVENTION

Posaconazole (CAS Registry Number 171228-49-2; CAS Name: 2,5-anhydro-1,3,4-trideoxy-2-C-(2,4-difluorophenyl)-4-[[4-[4-[4-[1-[(1S,2S)-1-ethyl-2-hydroxypropyl]-1,5-dihydro-5-oxo-4H-1,2,4-triazol-4-yl]phenyl]-1-piperazinyl]phenoxy]methyl]-1-(1H-1,2,4-triazol-1-yl)-D-threopentitol) which is represented by the following general formula (I)

(I)

is known as an antifungal agent. It is available as an oral suspension (40 mg/ml) under the trademark NOXAFIL® from Schering Corporation, Kenilworth, N.J.

WO95/17407 and WO 96/38443 disclose the compound having the general formula (I) and its use in treating fungal infections.

A pharmaceutical composition comprising posaconazole, at least one non-ionic surfactant and a diluent is disclosed in WO 02/80678, e.g. in the form of a liquid suspension. WO 02/80678 also describes that for use in its suspension posaconazole is to be micronized, e.g. by microfluidization to obtain a specific particle size in the range of about 1000 nm to about 1800 nm to obtain enhanced bioavailability. A solid solution of posaconazole, which can be provided in the form of a tablet or capsule, is disclosed in U.S. Pat. No. 5,972,381; other pharmaceutical compositions prepared by mixing or granulating posaconazole with a non-ionic surfactant and a diluent which may be formulated into capsules or tablets are disclosed in U.S. Pat. No. 5,834,472. A topical form of posaconazole, e.g., a lotion, cream, ointment, or "lacquer nail polish" is described in U.S. Pat. No. 4,957,730 (PENLAC® available from Dermik®). An injectable pharmaceutical suspension comprising posaconazole that is stable when subjected to terminal steam sterilization is disclosed in WO 2005/117831.

As was mentioned above, WO 95/17407 and WO 96/38443 disclose the compound having the general formula (I). However, during prosecution of the subsequently filed European patent application no. 98951994.7, now European patent number EP 1 021 439 B1, the applicant has declared that the methods disclosed in these publications only lead to the compound of formula I as an amorphous solid.

Polymorphism is a phenomenon relating to the occurrence of different crystal forms for one molecule. There may be several different crystalline forms for the same molecule with distinct crystal structures and distinct and varying physical properties like melting point, XRPD pattern, IR-spectrum and solubility profile. These polymorphs are thus distinct solid forms which share the molecular formula of the compound from which the crystals are made up, however, they may have distinct advantageous physical properties which can have a direct effect on the ability to process and/or manufacture the drug product, like flowability, as well as physical properties such as solubility, stability and dissolution properties which can have a direct effect on drug product stability, solubility, dissolution, and bioavailability.

Three polymorphic forms of posaconazole designated as forms I, II and III are described and characterized in WO 99/18097. Crystalline forms II and III were found to be unstable under the conditions investigated, so that crystalline form I was considered to be useful in the development of a pharmaceutical product.

SUMMARY OF THE INVENTION

The present inventors have found that crystalline forms II and III convert to a crystalline form, which is now designated as crystalline form Y, upon heating. They have surprisingly found that crystalline form Y is as stable as crystalline form I but has a better water solubility and thus is expected to have an improved rate and possibly also extent of absorption. Moreover, they have found that non-micronized crystalline form Y has a smaller mean and median particle size as well as a larger specific surface when compared to non-micronized crystalline form I so that crystalline form Y has an improved dissolution behaviour which in turn is expected to result in an improved bioavailability.

In one embodiment the present invention relates to a pharmaceutical composition comprising crystalline form Y of posaconazole and optionally at least one pharmaceutically acceptable additive.

Crystalline form Y of posaconazole can be described by an X-ray powder diffraction pattern comprising peaks at 2-theta angles of approximately 2.4°, 9.5°, 15.0°, 17.7°, and 23.7°. The typical precision of the 2-theta values is in the range of about ±0.2°.

Alternatively, crystalline form Y of posaconazole can be characterized by an attenuated total reflectance infrared spectrum comprising absorption bands at wavenumbers of about 3566, 2881, 2822, 1690, 1508, 1473, 1226, 1040, 947, 849 and 823 cm$^{-1}$. The typical precision of the wavenumber values is in the range of about ±2 cm$^{-1}$.

A further method of describing crystalline form Y is by differential scanning calorimetry. A typical differential scanning calorimetry curve of crystalline form Y has an onset temperature $T_{onset}$ between 167.5° C. and 171° C.

The pharmaceutical composition of the present invention can be used to treat or prevent fungal infections.

Other objects, features, advantages and aspects of the present invention will become apparent to those of skill from the following description. It should be understood, however, that the description and the following specific examples, while indicating preferred embodiments of the invention, are given by way of illustration only. Various changes and modifications within the spirit and scope of the disclosed invention will become readily apparent to those skilled in the art from reading the description and the other parts of the present disclosure.

DETAILED DESCRIPTION OF THE INVENTION

The present invention relates to a pharmaceutical composition comprising crystalline form Y of posaconazole.

Posaconazole is represented by the following general formula (I)

(I)

Crystalline form Y of posaconazole can be prepared by heating crystalline form II or crystalline form III at a temperature in the range of about 120° C. to about 150° C., preferably about 130° C. to about 150° C. and most preferably about 140° C. to about 145° C. Crystalline forms II and III can be obtained as described in WO 99/18097.

If desired, the crystalline material can be agitated during the heating step.

The duration of the heating step is not particularly limited. Generally, the heating will be conducted until substantially all (e.g., preferably at least 90 wt.-%, more preferably at least 95 wt.-%) of the crystalline form II or III has been converted into crystalline form Y. Typically for 1 g starting material the heating step will take from about 10 min to about 60 min, preferably from about 15 min to about 20 min. A skilled person can easily determine appropriate heating durations for other batch sizes.

After the heating step, the product is cooled to ambient temperature. Conversion to the form Y can be confirmed by IR or XRPD analysis as described herein.

The resultant crystalline form Y is a polymorphic form of posaconazole. Unlike form II which is a monohydrate and form III which is a non-stoichiometric hydrate, form Y is anhydrous like form I.

Figure 1:
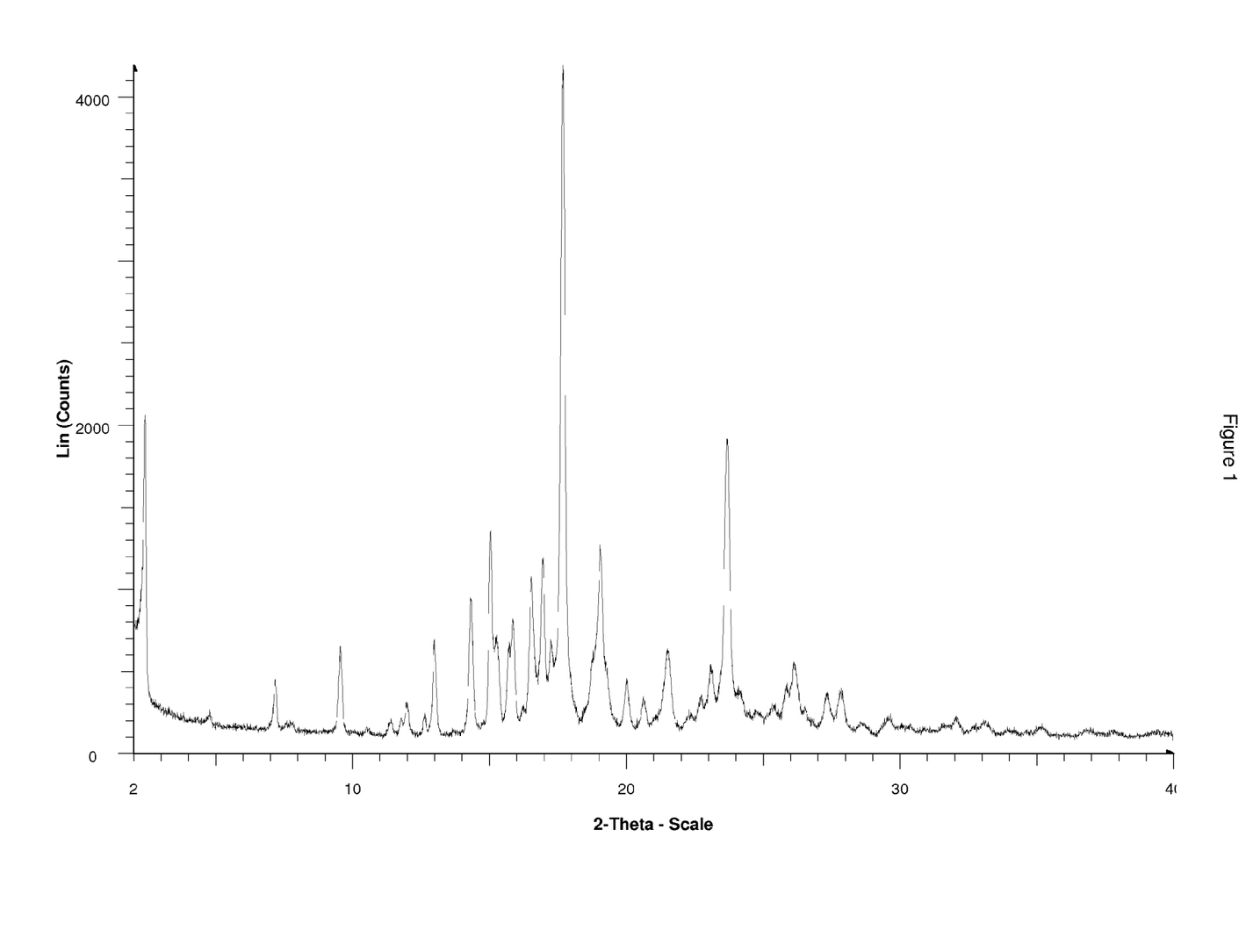
FIG. 1: X-ray powder diffraction pattern of form Y of posaconazole. In this figure the counts per 2 seconds (linear scale) are presented on the y-axis, while the 2 theta values in degrees are presented on the x-axis.

The crystalline form Y can be characterized by an X-ray powder diffraction pattern comprising peaks at 2-theta angles of approximately 2.4°, 9.5°, 15.0°, 17.7°, and 23.7° (about ±0.2°). A characteristic X-ray powder diffraction pattern is shown in FIG. 1.

Figure 2:
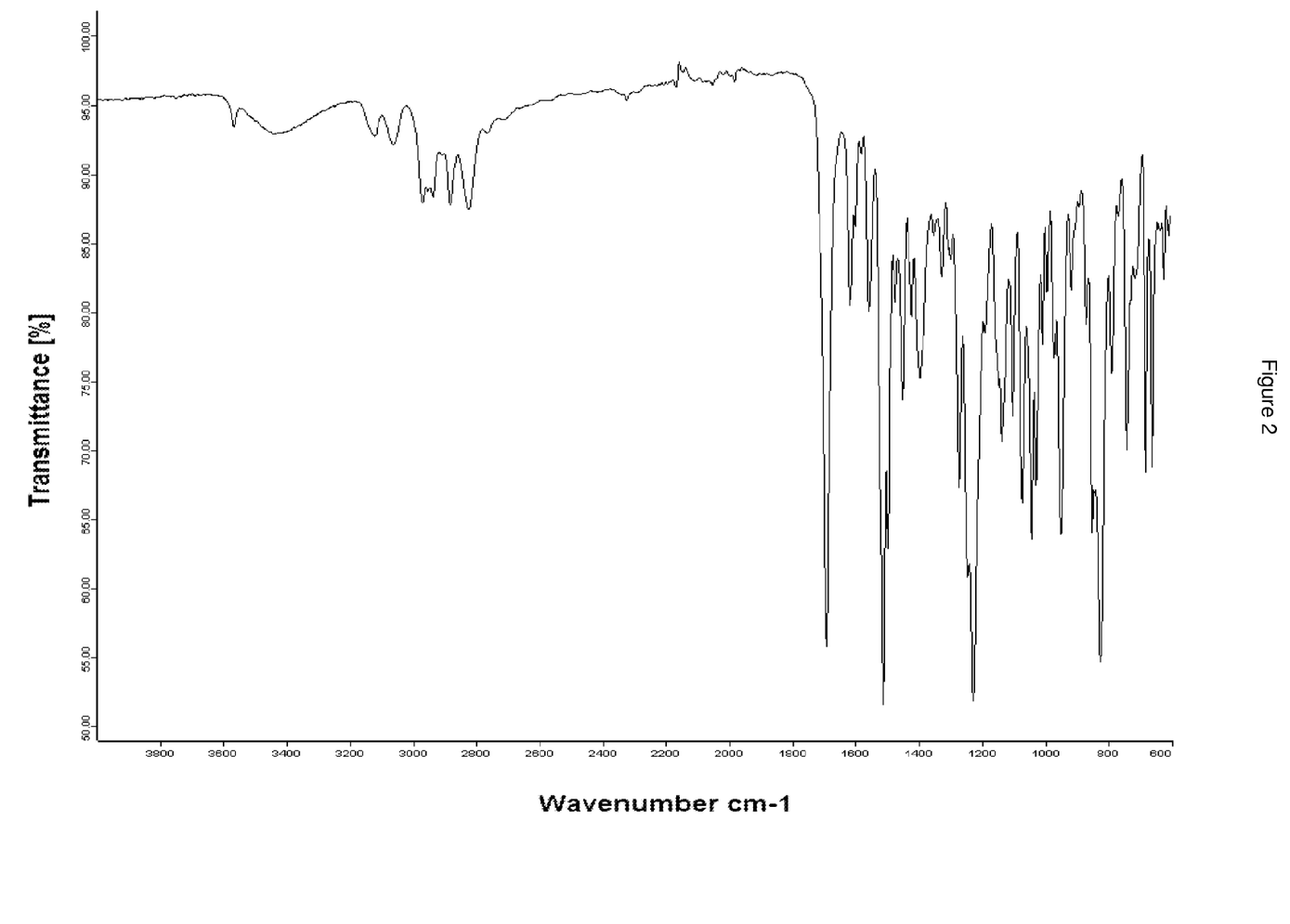
FIG. 2: Infrared spectrum of form Y of posaconazole. The transmittance in % is plotted versus the wavenumber in cm$^{-1}$.

Alternatively, crystalline form Y can be characterized by an attenuated total reflectance infrared spectrum comprising absorption bands at wavenumbers of about 3566, 2881, 2822, 1690, 1508, 1473, 1226, 1040, 947, 849 and 823 cm$^{-1}$ (about ±2 cm$^{-1}$). A typical attenuated total reflectance infrared spectrum is shown in FIG. 2.

Figure 3:
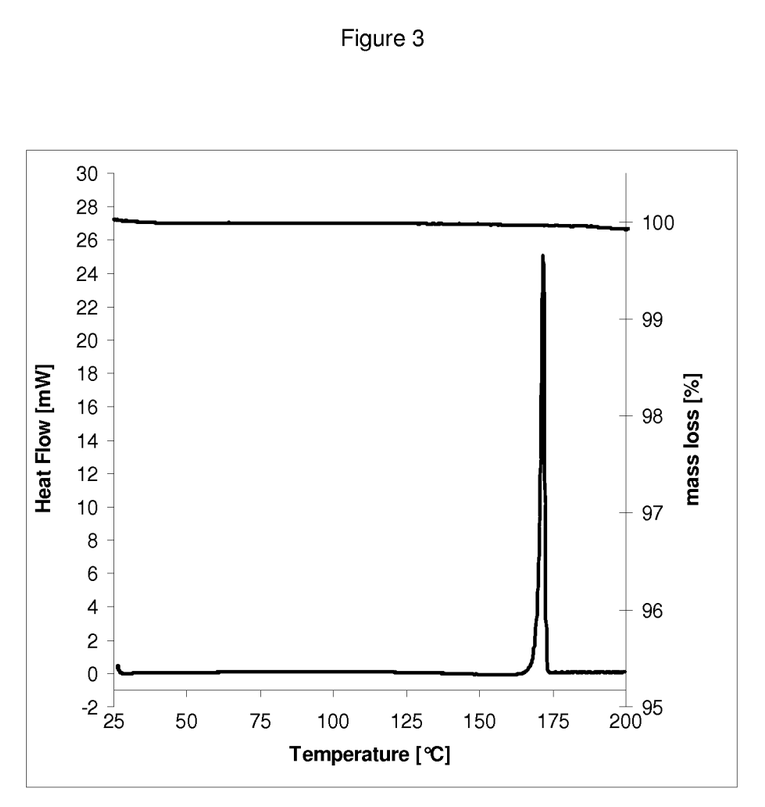
FIG. 3: Thermogravimetric and differential scanning calorimetric curve of form Y of posaconazole. The temperature in ° C. is shown on the x-axis. The heat flow in mW is shown on the left hand ordinate (lower curve), while the mass loss in is shown on the right hand ordinate (upper curve).

A further method for identifying crystalline form Y is differential scanning calorimetry. The onset temperature $T_{onset}$ is between 167.5° C. and 171° C. (10° C./minute, open pan). A characteristic curve is shown in FIG. 3.

The present inventors have surprisingly found that the new polymorph, crystalline form Y, is as stable as crystalline form I but has a water solubility that is about two times higher than that of crystalline form I. Since water solubility is an indication of the bioavailability, crystalline form Y is expected to have an improved rate and possibly also extent of absorption. This is especially important with posaconazole, because it is a highly lipophilic base (log P>3, pKa 3.6 and 4.6) and thus was previously limited in this respect.

Crystalline form Y is stable under storage conditions which are typical for pharmaceutical compositions and is thus suitable for the preparation of medicaments. Typical storage conditions are, for example, storage at ambient temperature, such as 25° C.±5° C., for several months (e.g., for at least 5 months, preferably at least 12 months, more preferably at least 24 months) in a closed vial.

Furthermore, crystalline form Y has proven to be stable under stress storage conditions, such as
(a) 140° C. for 3 days in a closed vial; or
(b) 100% relative humidity at 60° C. for 24 hours.

In this context, "stable" means that neither degradation nor polymorphic conversion to another polymorphic form of crystalline form Y can be detected, for example by HPLC, IR or XRPD analysis as defined herein.

Even if suspended in water and stirred for 4 days at ambient temperature, crystalline form Y of posaconazole is not susceptible to transformation into another form.

Moreover, even if suspended within a pharmaceutical composition, such as a liquid suspension as herein described, and stored for 7 weeks at room temperature, crystalline form Y of posaconazole shows polymorphic stability in the sense that no conversion to another polymorphic form is observed by measurement of the X-ray powder diffraction pattern as herein described (see also Example 6).

The specific surface of crystalline form Y of posaconazole as such, i.e. as obtained according to the herein described methods and in a non-micronized form, is typically about 4±1 $m^2/g$ as measured according to the known Multi-Point-BET-method as herein described and as shown in Example 8. This specific surface of crystalline form Y of posaconazole is more then twofold when compared to that of known crystalline form I. It is known that the specific surface between a solid and a liquid phase has direct impact on the dissolution rate and thus on the bioavailability of the pharmaceutical ingredient as described e.g. by the equation by Nernst and Brunner as found in W. Nernst, Z. Phys. Chem. 47 (1904), pp. 52-55. Therefore, as a higher specific surface results in a higher dissolution rate, crystalline form Y of posaconazole is expected to exhibit a better dissolution behaviour and consequently a better bioavailability when compared to crystalline form I. Indeed, Example 9 shows that non-micronized crystalline form Y of posaconazole—when contained in a suspension—shows a faster dissolution when compared to non-micronized form I.

The crystalline form Y of posaconazole can be used as a medicament, to treat or prevent any of the disorders which can be treated or prevented by posaconazole. In particular, crystalline form Y can be used for treating or preventing fungal infections, especially in mammals, such as humans. Thus, a method of treating or preventing a fungal infection by administering a therapeutically effective amount of crystalline form Y of posaconazole to a patient in need thereof is also contemplated. Crystalline form Y is suitable for treating or preventing a wide range of infections caused by fungal pathogens, including yeasts and molds. Typical fungal infections which can be treated or prevented are those caused by *Aspergillus*, *Blastomyces*, *Candida*, *Cryptococcus*, *Coccidioides*, *Epidermophyton*, *Fonsecaea*, *Fusarium*, *Mucor*, *Saccharomyces*, *Torulopsis*, *Trichophyton*, *Trichosporon*, *Sporothrix* and *Pneumocysitis*, particularly *Candida* and *Aspergillus*.

Typical fungal infections which can be treated or prevented are invasive infections, which most often occur in immunocompromised patients, such as organ transplant patients, cancer patients undergoing chemotherapy, hematopoietic stem cell transplant (HSCT) recipients with graft-versus-host disease (GVHD), patients with hematologic malignancies with prolonged neutropenia from chemotherapy. Examples of fungal infections which can be treated or prevented are oropharyngeal candidiasis, including oropharyngeal candidiasis refractory to itraconazole and/or fluconazole, fusariosis, chromoblastomycosis, mycetoma, coccidioidomycosis and invasive aspergillosis refractory to amphotericin B or itraconazole.

The crystalline form Y of posaconazole may thus be used for the preparation of a medicament for treating or preventing a fungal infection.

In one specific aspect of the invention, crystalline form Y of posaconazole may be used for the preparation of a medicament for treating or preventing a fungal infection wherein form Y of posaconazole has a specific surface of about 4±1 $m^2/g$.

Usually most of the posaconazole present in the pharmaceutical composition of the invention will be crystalline form Y although certain amounts of other crystalline forms or of amorphous posaconazole can also be present. Preferably at least about 90 wt.-%, more preferably at least about 95 wt.-%, even more preferably at least about 99 wt.-% and most preferably 100 wt.-% of the posaconazole present in the pharmaceutical composition is crystalline form Y.

Crystalline form Y of posaconazole can be administered alone or in combination with other pharmaceutically active compounds such as a further antifungal agent. In this case, the crystalline form Y of posaconazole and the other pharmaceutically active compound can be administered either simultaneously or sequentially.

The pharmaceutical composition comprising the crystalline form Y is not particularly limited and it can be formulated according to known principles, e.g. either alone or together with at least one pharmaceutically acceptable additive.

The crystalline form Y of posaconazole can be administered according to any appropriate route. Typically, the pharmaceutical composition will be adapted for oral, parenteral (SC, IM, IV and IP), topical or vaginal administration or administration by inhalation (orally or intranasally), preferably for oral, parenteral or topical administration.

Dosage forms for oral administration include tablets, capsules, lozenges, pills, wafers, granules, oral liquids such as syrups, suspensions, dispersions, solutions, emulsions, cachets, powders and powders for reconstitution.

Dosage forms for parenteral administration include solutions or emulsions for infusion, solutions, suspensions, dispersions or emulsions for injection, pre-filled syringes, and/or powders for reconstitution.

Dosage forms for local/topical administration comprise insufflations, aerosols, metered aerosols, transdermal therapeutic systems, medicated patches, solutions, suspensions, emulsions, lotions, creams or ointments suitable for application to the skin, rectal suppositories, and/or ovula.

The pharmaceutical compositions of the invention can be produced in a manner known per se to the skilled person as described, for example, in Remington's Pharmaceutical Sciences, 15th Ed., Mack Publishing Co., New Jersey (1991).

Pharmaceutical compositions according to the invention contain crystalline polymorph form Y as the active ingredient and optionally at least one pharmaceutically acceptable additive. Any pharmaceutically acceptable additive can be employed as long as it does not detrimentally affect the properties of the pharmaceutical composition. Examples of typical pharmaceutically acceptable additives comprise carriers (e.g., solid carriers such as magnesium carbonate, magnesium stearate, talc, sugar, lactose, pectin, dextrin, starch, gelatin, tragacanth, methylcellulose, sodium carboxymethyl-cellulose and wax; or liquid carriers such as water, aqueous or non-aqueous liquids), vehicles, diluents, solvents, binders, adjuvants, solubilizers, thickening agents, stabilizers, disintegrants, glidants, lubricating agents, buffering agents, emulsifiers, wetting agents, suspending agents, sweetening agents, colorants, flavors, coating agents, preservatives, antioxidants, processing agents, drug delivery modifiers, additives to make solutions isotonic, antifoaming agents, encapsulating material, surfactants (particularly non-ionic surfactants), opacifying agents, enhancers, waxes, cap anti-locking agents (e.g. glycerol) and ion exchange resins.

Other suitable pharmaceutically acceptable additives are described in Remington's Pharmaceutical Sciences, 15th Ed., Mack Publishing Co., New Jersey (1991).

The pharmaceutical composition may be a solid or liquid. Solid compositions include powders, tablets, dispersible granules, capsules, cachets, and suppositories. In this embodiment, the pharmaceutically acceptable additive can be one or more substances mentioned above and particularly be selected from carriers, diluents, flavoring agents, solubilizers, lubricants, suspending agents, binders or disintegrants. In powders, the additive can be a finely divided solid which is in admixture with the finely divided active compound. Suitable solid carriers are well-known in the art and include magnesium carbonate, magnesium stearate, talc, sugar, lactose, pectin, dextrin, starch, gelatin, tragacanth, methylcellulose, sodium carboxymethyl-cellulose and wax.

The pharmaceutically acceptable additive can also be an encapsulating material. The term "composition" is intended to include the formulation of the active ingredient with encapsulating material providing a capsule in which the active ingredient (with or without other additives) is surrounded by an encapsulating material, which is thus in association with it. Similarly, cachets are included. Tablets, powders, cachets and capsules can be used as solid dosage forms suitable for oral administration.

Topical formulations containing crystalline form Y normally contain one or more non-toxic, pharmaceutically acceptable topical carriers and may be in the form of e.g. a solution, suspension, emulsion, lotion, cream or ointment which is suitable for application to the skin of a mammal, in particular of a human patient. Topical formulations containing crystalline form Y which can be useful for nasal or ophthalmic administration are also contemplated. Ophthalmic formulations may also be ointments.

Typical formulations and indications for posaconazole are described, for example, in WO 95/17407, WO 96/38443, WO 02/80678, WO 2005/117831, WO 99/18097, U.S. Pat. No. 5,972,381, U.S. Pat. No. 5,834,472, and U.S. Pat. No. 4,957,730. It is to be noted that these patents and patent applications are given as an example only and that this list is not exhaustive.

Due to its enhanced water solubility crystalline form Y is especially suitable for liquid pharmaceutical formulations, in particular for oral administration such as suspensions or dispersions, e.g. aqueous suspensions or dispersions.

In one preferred embodiment, the pharmaceutical composition is in the form of an aqueous suspension or dispersion comprising crystalline form Y of posaconazole and a non-ionic surfactant and optionally at least one thickening agent. Examples of non-ionic surfactants and thickening agents are disclosed in WO 02/80678. As these thickening agents facilitate suspension of the pharmaceutical composition, they may also be considered as suspending agents. Additionally, the pharmaceutical composition may optionally contain further additives as mentioned herein and/or known for formulating liquid forms such as antifoaming agents, preservatives, opacifing agents, flavors, sweeteners, diluents, cap anti-locking agents and buffering agents. This pharmaceutical composition is preferably suitable for oral administration. Thus, in one specific embodiment, the pharmaceutical composition is an aqueous suspension or dispersion suitable for oral use which can be made by suspending or dispersing crystalline form Y of posaconazole (preferably having a particle size of about less than 100 μm, preferably of about less than 10 μm, preferably less than about 5 μm, e.g. 1.5±0.5 μm, or preferably having a median particle size of about 1.4±0.2 μm or of about 1.4±0.1 μm), a non-ionic surfactant, such as a sorbitan ester, and optionally at least one thickening agent, e.g. a combination of xanthan gum and a liquid sugar, in a pharmaceutically acceptable liquid carrier such as purified water.

The median particle size of crystalline form Y of posaconazole when used in a non-micronized form for preparing the pharmaceutical composition in the form of a liquid suspension as herein described, has been determined in samples taken from such suspension. Said median particle size is typically about 6±2 μm (micrometer) when measured with known laser diffraction methods, e.g. determination of the particle size distribution (Malvern) according to the USP <429> and EP 2.9.31. based on the diffraction of laser by particles within the measurement volume (for details see Example 7).

The mean particle size of crystalline form Y of posaconazole is typically about 10±2 μm ($D_{4,3}$ value) when measured as indicated above.

Therefore and surprisingly, crystalline form Y of posaconazole as such—i.e. in its non-micronized form—shows a smaller mean and median particle size when compared to non-micronized prior art posaconazole polymorphic forms such as form I. This smaller particle size of crystalline form Y of posaconazole—in particular in combination with its higher specific surface value—advantageously leads to an improved dissolution behaviour of crystalline form Y of posaconazole, e.g. when contained in a pharmaceutical composition such as a suspension, e.g. leads to a faster dissolution of form Y of posaconazole when compared to that of known form I as shown in Example 9. This improved dissolution behaviour of crystalline form Y of posaconazole is expected to result in better bioavailability when compared to suspensions containing known non-micronized polymorphic form I.

Therefore, crystalline form Y of posaconazole may be used for the preparation of a medicament for treating or preventing a fungal infection wherein crystalline form Y of posaconazole has a mean particle size of about 10±2 μm and/or a median particle size of about 6±2 μm.

In one preferred embodiment of the invention, crystalline form Y of posaconazole is micronized in order to obtain a mean and/or median particle size as described e.g. in WO 02/80678, e.g. may be micronized according to known methods such as microfluidization, e.g. as described in U.S. Pat. No. 4,533,254. Such micronized crystalline form Y of posaconazole may have a median particle size range of about 1000 nanometers (nm) to about 1800 nm, e.g. about 1200 nm to about 1600 nm. Preferably, the median of the particles shows a size of about 1.4±0.2 μm or about 1.4±0.1 μm. Alternatively, crystalline form Y of posaconazole may be micronized by known milling methods.

Even if crystalline form Y will be micronized to obtain the above described particle size, due to its originally smaller particle size, advantageously, less steps, time and costs for micronization, e.g. by microfludization techniques will be required when compared micronization of known form I.

One specific example of a pharmaceutical composition in the form of a liquid suspension within the scope of the invention is described below:

Example A

| Ingredient | Concentration in mg/ml |
| --- | --- |
| Posaconazole Form Y | 40 |
| Polysorbate 80 | 10 |
| Sodium Citrate dihydrate | 0.6 |
| Citric Acid monohydrate | 1.5 |
| Simethicone | 3 |
| Xanthan gum | 3 |
| Sodium benzoate | 2 |
| Liquid glucose | 350 |
| Glycerol | 100 |
| Artificial cherry flavour | 5 |
| Titanium dioxide | 4 |
| Purified water, q.s. | Ad 1 ml |

A suspension such as that of Example A may be prepared as follows:
about 40% of the final amount of Polysorbat 80 and about 40% of the final amount of Simethicon are mixed and dissolved and/or dispersed in about 12% of the final amount of purified water and homogenized with Ultra Turrax (as commercially available from IKA Werke GmbH, Germany). Subsequently, posaconazole is suspended or dispersed in this mixture under homogenization by Ultra Turrax. The remaining about 60% of Polysorbat 80 and of Simethicon and about 32% of the final amount of the purified water are added and mixed and optionally homogenized using Ultra Turrax, followed by the addition of sodium benzoate, sodium citrate dihydrate and citric acid monohydrate. After further mixing, xanthan gum is added followed by mixing, e.g. by magnetic stirring, and a hydratization phase without any mixing. Subsequently, glycerol, liquid glucose and titanium dioxide are added under continuous mixing optionally using additionally a suitable homogenizer. Finally, cherry flavour and the remaining portion of about 56% of the final amount of purified water are added and mixed until a uniform suspension is obtained.

In a preferred embodiment, posaconazole Form Y is micronized when used in the above described composition to have a median particle size in the range of about 1 μm to about 1.8 μm, e.g. about 1.2 μm to about 1.6 μm, preferably of about 1.4±0.2 μm or about 1.4±0.1 μm.

In another embodiment, the pharmaceutical composition is in a solid form, e.g. in the form of a powder or of granules, which might be used to prepare a liquid form, such as a suspension or dispersion as described herein.

Parenteral forms to be injected intravenously, intramuscularly, or subcutaneously may generally be in the form of a sterile solution, and may contain additives such as salts or glucose to make the solution isotonic.

The dosage of crystalline form Y of posaconazole can be determined by a skilled physician and will depend on various factors such as the disorder to be treated, its severity, the mode of administration, the sex, age and weight of the patient, etc. Typically about 1 to about 30 mg/kg body weight per day, more typically about 1 to about 20 mg/kg bodyweight per day, even more typically about 1 to about 10 mg/kg bodyweight per day will be given for oral administration, while from about 0.25 mg/kg body weight per day to about 20 mg/kg body weight per day, preferably from about 0.5 mg/kg body weight per day to about 10 mg/kg body weight per day, will be applied via parenteral administration.

The amount of crystalline form Y within topical formulations can vary. It will typically be from about 0.1% to about 20%, preferably about 0.5% to about 10%, by weight of the total pharmaceutical composition.

The amount of crystalline form Y of posaconazole within the liquid pharmaceutical compositions for oral administration described above can also vary. It may be from about 10 mg/ml to about 100 mg/ml, preferably from about 20 mg/ml to about 60 mg/ml, and e.g. be about 40 mg/ml.

Antifungally effective amounts of the liquid pharmaceutical compositions for oral administration described above and containing e.g. 40 mg/ml of crystalline form Y of posaconazole may be administered orally in doses of 5 ml containing 200 mg of crystalline form Y of posaconazole—three times a day or four times a day—, or in doses of 10 ml containing 400 mg of crystalline form Y of posaconazole—twice a day. The attending physician may change the doses and dosing regimen in view of the age, health and sex of the patient as well as the severity of the disease.

The pharmaceutical compositions will be typically administered daily.

The present invention is illustrated by the following examples, which should not be construed as limiting.

EXAMPLES

The X-ray powder diffraction pattern (XRPD) was obtained with a PANalytical X'Pert PRO diffractometer equipped with a theta/theta coupled goniometer in transmission geometry, Cu-K$\alpha_{1,2}$ radiation (wavelength 0.15419 nm) with a focusing mirror and a solid state PIXcel detector. The patterns were recorded at a tube voltage of 40 kV, tube current of 40 mA, applying a stepsize of 0.006° 2θ with 80 s per step in the angular range of 2° to 40° 2θ at ambient conditions. A typical precision of the 2-theta values is in the range of about ±0.2° 2-theta. Thus a diffraction peak that appears at 5.0° 2-theta can appear between 4.8 and 5.2° 2-theta on most X-ray diffractometers under standard conditions.

Infrared spectra (IR) were collected on a MKII Golden Gate™ Single Reflection Diamond ATR (attenuated total reflection) cell with a Bruker Tensor 27 FTIR spectrometer with 4 cm$^{-1}$ resolution. To collect a spectrum a spatula tip of a sample was applied to the surface of the diamond in powder form. Then the sample was pressed onto the diamond with a sapphire anvil and the spectrum was recorded. A spectrum of the clean diamond was used as background spectrum. A typical precision of the wavenumber values is in the range of about ±2 cm$^{-1}$. Thus, an infrared peak that appears at 1716 cm$^{-1}$ can appear between 1714 and 1718 cm$^{-1}$ on most infrared spectrometers under standard conditions.

Differential scanning calorimetry (DSC) was performed with a DSC 7 (Perkin-Elmer, Norwalk, Conn., USA) using the Pyris software. A sample of about 4 mg was weighed into a 25 μl Al-pan. Dry nitrogen was used as the purge gas (purge: 20 ml min$^{-1}$). When used herein, the term "$T_{onset}$" determined by Differential Scanning calorimetry means the temperature corresponding to the intersection of the pretransition baseline with the extrapolated leading edge of the transition.

Thermogravimetric analysis was performed with the thermogravimetric system TGA-7 using the Pyris Software for Windows NT (Perkin-Elmer, Norwalk, Conn., USA), 50 μl platinum pans, nitrogen purge gas (sample purge: 20 ml min⁻¹, balance purge: 40 ml min⁻¹).

Melting points were determined with a Büchi B-545 instrument in automatic mode with a threshold of 40% transmission. Measurements were conducted in pharmacopeia mode at 1.0° C./min heating rate.

The moisture sorption isotherm was recorded with a SPS-11 moisture sorption analyzer (MD Mess-technik, Ulm, D). The measurement cycle was started at 0% relative humidity (RH), increased in 10% steps up to 90% RH and in a 5% step up to 95% RH. The equilibrium condition for each step was set to a constant mass ±0.003% over 49 min. The temperature was 25±0.1° C.

HPLC assay was performed by applying the following conditions:

Column: ZORBAX XDB-C18 Rapid Resolution HT, 1.8 μm, 50×4.6 mm (Agilent Technologies)
Eluent A: Dilute 2 ml of acetic acid (99-100%) with water and fill up to 1000 ml with water. Adjust pH to 6.5 with 2.5% ammonia.
Eluent B: water/acetonitrile=50/50 (v/v)
Flow rate: 0.8 ml/min
Temperature: 40° C.
Detection: UV at 260 nm
Gradient:

|  | t [min] | | |
| --- | --- | --- | --- |
|  | 0 | 7.5 | 20 |
| % B | 35 | 85 | 95 |

Stop time: 20 min
Post time: 5 min
Sample concentration: about 0.5 mg/ml
Solvent: water/acetonitrile=50/50 (v/v)

Example 1

Preparation of crystalline form Y of Posaconazole by Heating Monohydrate Form II 1 g monohydrate form II of posaconazole was placed in a 140° C. preheated Büchi Kugelrohr apparatus and agitated for 15 min. The anhydrous product obtained was cooled and analyzed by DSC, XRPD and IR. The product obtained was the new anhydrous polymorph form Y of posaconazole.

The melting point of the product of Example 1 was 169.9±0.1° C.

The $T_{onset}$ of form Y in the DSC curve, the product of Example 1, was 170.3° C. (10° C./minute, open pan) without any transformation at lower temperature (FIG. 3).

The powder X-ray diffraction pattern of the product of Example 1 is shown in FIG. 1. The characteristic XRPD angles, d-spacings and relative intensities are shown in Table 1.

The form Y of posaconazole obtained above has an IR spectrum with peaks at 3566, 2881, 2822, 1690, 1508, 1473, 1226, 1040, 947, 849 and 823 cm⁻¹ as is shown in FIG. 2.

TABLE 1

Angles 2-theta, d-values and relative intensities of form Y

| Angle [2-Theta] | d value [Angstrom] | rel. intensity [%] |
| --- | --- | --- |
| 2.4 | 36.983 | 40 |
| 4.8 | 18.585 | 3 |
| 7.2 | 12.347 | 8 |
| 9.5 | 9.267 | 13 |
| 11.4 | 7.780 | 2 |
| 11.9 | 7.403 | 5 |
| 12.6 | 7.009 | 4 |
| 13.0 | 6.817 | 15 |
| 14.3 | 6.183 | 20 |
| 15.0 | 5.891 | 30 |
| 15.8 | 5.589 | 16 |
| 16.5 | 5.361 | 22 |
| 16.9 | 5.229 | 25 |
| 17.2 | 5.138 | 12 |
| 17.7 | 5.015 | 100 |
| 19.1 | 4.655 | 27 |
| 20.0 | 4.434 | 7 |
| 20.6 | 4.305 | 5 |
| 21.5 | 4.130 | 12 |
| 23.7 | 3.753 | 43 |

Example 2

The Preparation of Crystalline Polymorph Form Y of Posaconazole by Heating Form III 1 g form III of posaconazole was heated to 140° C. as in Example 1 for 15 min yielding the new anhydrous form Y. This was confirmed by IR and XRPD analysis.

Example 3

The Solid State Stability of Form Y

The solid state stability of form Y was determined by storing approximately 1.0 g of the material in a glass bottle at a) 60° C./100% Relative Humidity (RH), open exposure, for 24 hours and b) at 140° C., closed, for 3 days.

The material was assayed by HPLC for final content and degradation products.
a) 60° C./100% RH: No significant degradation observed (HPLC assay 99.9% initial).
b) 140° C.: No significant degradation observed (HPLC assay 99.9% initial).

Figure 4:
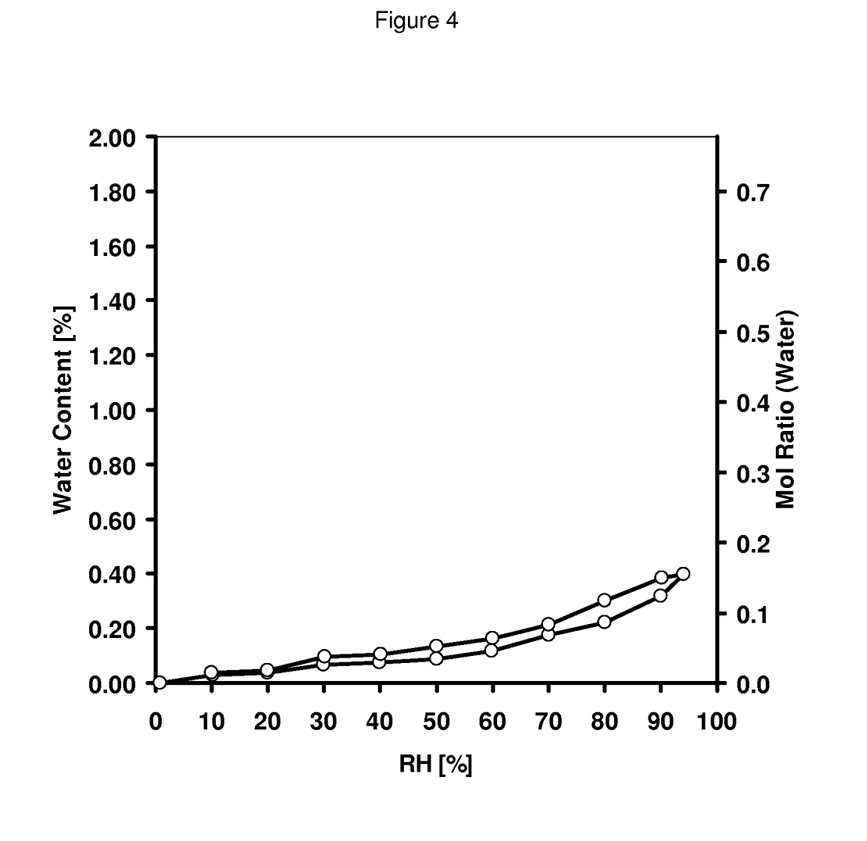
FIG. 4: Moisture sorption isotherm of form Y of posaconazole. The water content in (left hand ordinate) and the mol ratio of water (right hand ordinate) are plotted versus the relative humidity in %. The lower line refers to sorption, while the upper line refers to desorption.

In the case of a), when the form Y was left for 24 hours at 100% RH, temperature 60° C., form Y was not converted into another polymorphic form. The moisture sorption isotherm of form Y shows that the water uptake does not exceed 0.4% (FIG. 4).

Example 4

The Stability of an Aqueous Suspension of Form Y 120 mg form Y were suspended in 3 ml water and the suspension was stirred at room temperature. The physicochemical properties of the solid after stirring for 4 days were the same as the physicochemical properties of form Y obtained in Example 1.

Example 5

The Solubility of the Form Y

The solubility of form Y was determined by the equilibrium solubility method, which employed a saturated solution of form Y, obtained by stirring 250 mg form Y in 6 ml water over night. The sample was filtered through a 0.45 μm membrane filter and the concentration of form Y in the filtrate was measured using a Perkin Elmer Lambda 35 UV/VIS spectrophotometer (λ=260 nm). The solubility of form Y was found to be 1.5 μg/ml which is about two times higher than that of form I.

Example 6

The Stability of Form Y Within a Pharmaceutical Formulation 25 ml of a suspension containing form Y were prepared as follows:

| Ingredient | Quantity (in g) |
|---|---|
| Posaconazole Form Y | 1.0 |
| Polysorbate 80 | 0.3 |
| Simethicone | 0.1 |
| Xanthan gum | 0.1 |
| Sodium benzoate | 0.1 |
| Liquid glucose | 8.8 |
| Glycerol | 2.5 |
| Purified water | 15.7 |

40% of the final amount of Polysorbat 80 and 40% of the final amount of simethicon were mixed and dissolved and/or dispersed in about 12% of the final amount of purified water and homogenized with Ultra Turrax (30 seconds; 27,000 rpm). Subsequently, 1 g of form Y of posaconazole were suspended or dispersed in this mixture under homogenization by Ultra Turrax (27,000 rpm, 2 minutes). The remaining 60% of Polysorbat 80 and of simethicon and 32% of the final amount of the purified water were added and mixed followed by the addition of sodium benzoate, sodium citrate dehydrate and citric acid monohydrate. After further mixing, xanthan gum was added to the mixture under stirring, followed by a 30 minutes phase of hydratization without mixing. Subsequently, glycerol and liquid glucose and of the remaining portion of 56% of the final amount of purified water were added under mixing until a uniform suspension was obtained.

This suspension was stored at room temperature for 7 weeks. A sample of approximately 1 g of the suspension was dried under vacuum over night at room temperature. An X-ray powder diffractogram was collected from dried formulation and revealed only peaks of form Y, thus indicating that no conversion to another polymorphic form had occurred. Diffractograms for this example were collected with a Unisantis XMD 300 X-ray powder diffractometer with a position sensitive detector in parallel beam optics, using a Cu anode with 40 kV and 0.8 mA, from 3-43° 2-Theta with simultaneous detection of regions of 10° per step with detector resolution 1024 and a counting time of 300 seconds per step.

Example 7

Determination of Median and Mean Particle Size of Form Y

Crystalline form Y in a non-micronized form as obtained by Example 1 was used to prepare 25 ml of a suspension as follows:

| Ingredient | Quantity (in g) |
|---|---|
| Posaconazole Form Y | 1.000 |
| Polysorbate 80 | 0.250 |
| Simethicone | 0.075 |
| Xanthan gum | 0.075 |
| Sodium benzoate | 0.050 |
| Sodium Citrate Dihydrate | 0.015 |
| Citric Acid Monohydrate | 0.038 |
| Liquid glucose | 8.750 |
| Glycerol | 2.500 |
| Titanium dioxide | 0.100 |
| Cherry Flavour #13174 | 0.125 |
| Purified water | 15.498 |

The suspension was prepared analogously to the method described in Example 6 up to and including the addition of glycerol and liquid glucose. Subsequently, titanium oxide was added under mixing with a suitable homogenizer, followed by the addition of the cherry flavour and of the remaining portion of 56% of the final amount of purified water under mixing until a uniform suspension was obtained.

25 ml of a similar suspension, but without cherry flavour and using 12.148 g of purified water, was prepared analogously using non-micronized crystalline form I of posaconazole.

The particle size distribution (Malvern) was measured according to the USP <429> and EP 2.9.31. based on the diffraction of laser by particles using a Mastersizer 2000S liquid dispersion system. The particle size measurement was started after ultrasonic treatment of the sample for 5 min. The results are shown in Table 2 below:

TABLE 2

| Polymorphic form of posaconazole in non-micronized form | Median particle size (d (0.5)-value in μm) | Mean particle size ($D_{4,3}$-value in μm) |
|---|---|---|
| Crystalline Form Y | 6.0 | 9.9 |
| Crystalline Form I | 31.3 | 35.1 |

Table 2 shows that non-micronized crystalline form Y has an about 5-fold smaller median particle size and an about 4-fold smaller mean particle size when compared to non-micronized form I. This smaller particle size, in particular the smaller mean particle size of crystalline form Y results in an improved dissolution behaviour, i.e. a faster dissolution of form Y when compared to form I—as is indeed shown in Example 9 below. This improved dissolution of crystalline form Y is generally considered to lead to an improved bioavailability.

Example 8

Determination of the Specific Surface of Crystalline Form Y

Specific surface measurement was performed with the equipment NOVA 2000 as commercially available from Quantachrome Instruments using the BET method and Nitrogen as the absorbed gas at 77° K (i.e. −196.15° C.) as described e.g. by Medema J, Campagne A.: A Simple Method to Determine Cumulative Surface-Area Distributions of Porous Solids; Journal of Catalysis, Volume 8, Issue 2, pp. 120, 1967. The results are shown in Table 3 below:

TABLE 3

| Specific Surface (in m²/g) | |
| --- | --- |
| Crystalline Form Y of posaconazole | Crystalline Form I of posaconazole |
| 3.6 | 1.5 |
| 3.7 | 1.6 |

Table 3 shows that crystalline form Y of posaconazole has an about 2.4-fold larger specific area when compared to crystalline form I of posaconazole. As explained above, this higher specific surface value results in a higher dissolution rate which is expected to lead to an improved bioavailability of form Y when compared to that of known form I.

Example 9

Dissolution of Crystalline Form Y as Compared to Form I

Non-micronized form Y and non-micronized form I were incorporated into formulations having compositions and being prepared according to Example 7.

Dissolution of Form Y and Form I from those formulations was tested according to USP 32 (2009) method <711> (USP apparatus II (Paddle); 25 rpm; dissolution medium: 0.3% SLS aqueous solution). Posaconzole concentrations were determined with an online photometer (UV absorption at 260 nm). Crystalline non-micronized form Y of posaconazole showed a clearly faster dissolution compared to that of non-micronized form I as was expected based on the smaller particle size and the higher specific area value of form Y when compared to form I.

The invention claimed is:

1. A pharmaceutical composition comprising crystalline form Y of posaconazole and optionally at least one pharmaceutically acceptable additive, wherein the crystalline form Y of posaconazole has at least one of an X-ray powder diffraction pattern comprising peaks at 2-theta angles of approximately 2.4°±0.2°, 9.5°±0.2°, 15.0°±0.2°, 17.7°±0.2°, and 23.7°±0.2° or an attenuated total reflectance infrared spectrum comprising absorption bands at wavenumbers of about 3566±2 $cm^{-1}$, 2881±2 $cm^{-1}$, 2822±2 $cm^{-1}$, 1690±2 $cm^{-1}$, 1508±2 $cm^{-1}$, 1473±2 $cm^{-1}$, 1226±2 $cm^{-1}$, 1040±2 $cm^{-1}$, 947±2 $cm^{-1}$, 849±2 $cm^{-1}$ and 823 $cm^{-1}$±2 $cm^{-1}$.

2. The pharmaceutical composition according to claim 1, wherein the crystalline form Y of posaconazole has an X-ray powder diffraction pattern substantially in accordance with FIG. 1.

3. The pharmaceutical composition according to claim 1, wherein the crystalline form Y of posaconazole has an attenuated total reflectance infrared spectrum substantially in accordance with FIG. 2.

4. The pharmaceutical composition according to claim 1, wherein the crystalline form Y of posaconazole has a median particle size of about 6±2 μm.

5. The pharmaceutical composition according to claim 1, wherein the crystalline form Y of posaconazole has a specific surface of about 4±1 m²/g.

6. The pharmaceutical composition according to claim 1, wherein the composition is in the form of an aqueous suspension or dispersion comprising a non-ionic surfactant and optionally at least one thickening agent.

7. The pharmaceutical composition according to claim 1, formulated for treating a fungal infection.

8. A medicament comprising crystalline form Y of posaconazole according to claim 1.

9. The pharmaceutical composition according to claim 1, wherein the crystalline form Y of posaconazole has a mean particle size of about 10±2 μm.

* * * * *